United States Patent
Hopps

(10) Patent No.: US 9,936,731 B2
(45) Date of Patent: Apr. 10, 2018

(54) AEROSOL-GENERATION DEVICES

(71) Applicant: JT International S.A., Geneva (CH)

(72) Inventor: Jason Hopps, Coleraine (GB)

(73) Assignee: JT International SA (CH)

( * ) Notice: Subject to any disclaimer, the term of this patent is extended or adjusted under 35 U.S.C. 154(b) by 307 days.

(21) Appl. No.: 14/390,150

(22) PCT Filed: Jan. 21, 2013

(86) PCT No.: PCT/EP2013/051011
§ 371 (c)(1),
(2) Date: Oct. 2, 2014

(87) PCT Pub. No.: WO2013/152873
PCT Pub. Date: Oct. 17, 2013

(65) Prior Publication Data
US 2015/0047662 A1  Feb. 19, 2015

(30) Foreign Application Priority Data

Apr. 12, 2012 (EP) .................................. 12163871

(51) Int. Cl.
*A24F 47/00* (2006.01)
*A61M 11/04* (2006.01)
*A61M 15/06* (2006.01)
*A61M 15/00* (2006.01)
*H05B 1/02* (2006.01)

(52) U.S. Cl.
CPC ......... *A24F 47/008* (2013.01); *A61M 11/041* (2013.01); *A61M 11/042* (2014.02); *A61M 15/0003* (2014.02); *A61M 15/06* (2013.01); *H05B 1/0252* (2013.01); *A61M 2205/3653* (2013.01); *A61M 2205/8206* (2013.01); *Y10T 137/87571* (2015.04)

(58) Field of Classification Search
CPC .. A61L 9/035; B05B 12/1418; B05B 11/3083
USPC ...................................... 239/61–62
See application file for complete search history.

(56) References Cited

U.S. PATENT DOCUMENTS 4,050,629 A * 9/1977 Query ................... A01M 13/00
                                                     137/78.2
4,141,369 A * 2/1979 Burruss ..................... A24F 1/00
                                                     128/203.27

(Continued)

FOREIGN PATENT DOCUMENTS

EP        2022349 A1      2/2009
WO   WO 2011120085 A1 * 10/2011 ........... B67D 3/0009

OTHER PUBLICATIONS

International Search Report for PCT/EP2013/051011, dated May 24, 2013, 5 pages.

*Primary Examiner* — Eric Yaary
(74) *Attorney, Agent, or Firm* — Lerner, David, Littenberg, Krumholz & Mentlik, LLP

(57) ABSTRACT

An aerosol generating device comprises two reservoirs, each arranged to contain a separate aerosol producing composition; means for drawing the compositions from the reservoirs to generate an aerosol for inhalation for a user, and means for mixing the compositions after they have been drawn from the reservoirs, the mixing means being arranged to allow a user to select the relative proportions of the two compounds in the aerosol.

12 Claims, 6 Drawing Sheets

(56) References Cited

U.S. PATENT DOCUMENTS

| | | | |
|---|---|---|---|
| 4,945,928 A * | 8/1990 | Rose | A24B 15/165 131/270 |
| 2007/0062548 A1 | 3/2007 | Horstmann et al. | |
| 2007/0267031 A1 * | 11/2007 | Hon | A24F 47/008 131/273 |
| 2009/0126722 A1 * | 5/2009 | Sugita | A61K 9/0073 128/200.19 |
| 2010/0108779 A1 * | 5/2010 | Filsouf | B05B 11/0054 239/61 |
| 2010/0200008 A1 | 8/2010 | Taieb | |
| 2010/0243754 A1 * | 9/2010 | Harris | A01M 1/2033 239/34 |
| 2010/0319686 A1 | 12/2010 | Schennum | |
| 2011/0011396 A1 * | 1/2011 | Fang | A24F 47/008 128/202.21 |
| 2011/0232654 A1 | 9/2011 | Mass | |
| 2011/0265806 A1 * | 11/2011 | Alarcon | A24F 47/00 131/273 |
| 2012/0048266 A1 * | 3/2012 | Alelov | A61M 11/005 128/202.21 |
| 2012/0279990 A1 * | 11/2012 | Werner | B05B 11/3083 222/132 |
| 2013/0104916 A1 * | 5/2013 | Bellinger | A61M 11/041 131/328 |

* cited by examiner

AEROSOL-GENERATION DEVICES

CROSS REFERENCE TO RELATED APPLICATION

The present application is a national stage application under 35 U.S.C. § 371 of International Application No. PCT/EP2013/051011, filed Jan. 21, 2013, published in English, which claims priority from European Patent Application No. 12163871.2, filed Apr. 12, 2012, all of which are incorporated by reference herein in their entireties.

The present invention relates to aerosol-generating devices, in particular electronic cigarettes.

Traditional approaches to generating aerosol often do not use heat energy, and include pressurised containers with valves, dry powder formulations or nebulisers.

Electronic cigarettes are relatively well known in the art and are becoming popular as a substitute for a regular cigarette. The most common operating principle for such electronic cigarettes is to provide a flavoured aerosol to a user without burning material. Such an aerosol can comprise inhalable mixtures of gases, liquid aerosols (liquid particles suspended in air) and/or solid aerosols (solid particles suspended in air). One of the most common approaches to providing the flavoured aerosol is to have a reservoir of aerosol-generating liquid which is vaporised by provision of an electrically powered heat source to which the liquid is provided.

Aerosol-generating liquids typically contain, in varying proportions, at least one aerosol producer (often propylene glycol and/or glycerol), diluents (water and/or ethanol), flavours and/or tobacco extracts, and aroma compounds.

Some prior art electronic cigarettes operate through a user depressing a switch which activates the heating process after which they can inhale from the electronic cigarette. Others have an activation switch for the heater which is operated when a user inhales and draws air through the electronic cigarette.

Whilst such electronic cigarettes are becoming popular, consumers seem to experience some problems with them. For example, it can be difficult for the user to control the level of intensity or strength of flavour that is delivered to them. Attempts have been made to overcome this by having a control over the element that creates the aerosol, but such devices often provide such low level of aerosol at some settings that consumers dislike them.

Furthermore, some compounds in the aerosol-generating liquid that are used to provide flavour to the aerosol can lose aroma character over time. As an example, vanillin, a vanilla flavour component, reacts with propylene glycol when mixed, reducing the flavour generated by the vanillin and also producing a deep red discolouration in the aerosol-generating liquid.

The present invention seeks to provide an aerosol generating device which overcomes at least some of the above problems.

According to the present invention there is provided an aerosol generating device comprising:
  at least two reservoirs, each arranged to contain a separate aerosol producing composition;
  means for drawing the compositions from the reservoirs to generate an aerosol for inhalation for a user, and
  means for mixing the compositions after they have been drawn from the reservoirs, the mixing means being arranged to allow a user to select the relative proportions of the two compounds in the aerosol.

In a preferred embodiment of the invention the aerosol generating device is an electronic cigarette and comprises:
  a power source;
  at least one heater assembly;
  a means for selectively applying power from the power source to the heater assembly;
  at least two liquid-containing reservoirs, each arranged to contain a separate aerosol producing composition; and
  control means for selectively controlling the heating of liquid from one or more of the reservoirs by the heater assembly, such that, when power is supplied to the heater assembly together with the selected liquid, an aerosol is generated for inhalation by a user.

With the present invention, it is possible for a user to control the content of the aerosol that they receive by controlling the source of the liquid.

This control may also allow the mixing of components during aerosol generation such that they are not mixed in advance and therefore not subject to adverse aging effects.

Examples of the present invention will now be described with reference to the accompanying drawings, in which.

Figure 1:
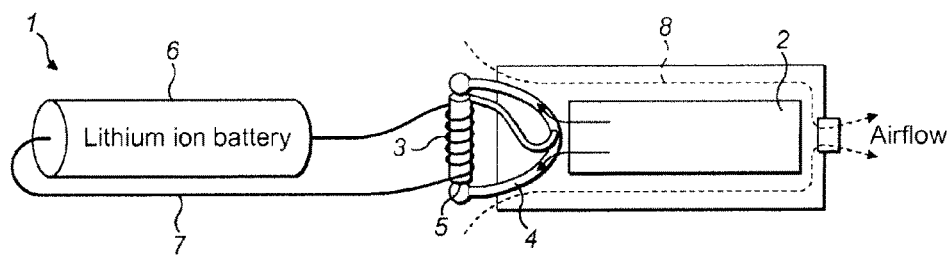
FIG. 1 is a schematic diagram showing a conventional electronic cigarette.

Referring to FIG. 1 an example prior art electronic cigarette 1 has a liquid reservoir 2 containing an aerosol-generating liquid. The liquid reservoir 2 is fluidly connected to a heater assembly 3, the fluid connection in this example being provided by a porous metal bridge 4 (for example, foamed nickel) and a transfer element 5. The transfer element 5 typically operates by capillary action, and can take various physical forms, such as heat-resistant fibres of glass or ceramic, narrow-diameter capillary tubes or various other porous materials. The heater assembly 3 comprises a heating filament connected to a battery 6 via a switch 7 to heat the transfer element 5 such that a liquid transferred by capillary action in the transfer element 5 is vaporised at its surface under heat conduction from the heater assembly 3 to the transfer element 5. In operation the switch 7 is activated either by depression by a user or by detection of air being drawn through the electronic cigarette 1 by a user. This enables the supply of current from the battery 6 to the heater assembly 3 which heats and vaporises liquid in the transfer element 5 which then passes into the air stream 8 within the electronic cigarette 1 and out through to a user for inhalation.

Figure 2:
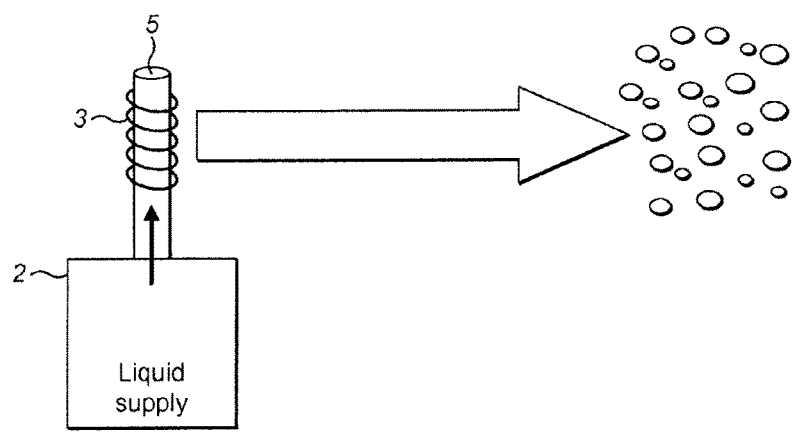
FIG. 2 is a schematic diagram showing the operation of a conventional electronic cigarette.

FIG. 2 shows some of the key components of FIG. 1 to explain in more detail operation of an electronic cigarette. Here the liquid reservoir 2 supplies liquid via a capillary action to the transfer element 5, the transfer element 5 being selectively heated by the heater assembly 3. Air flow over the transfer element 5 is indicated by the arrows which show how air is drawn over the transfer element 5, the heater assembly 3 then heating a very small (but constant) quantity of the liquid and boiling it into gas to generate an aerosol which is delivered to a user. With appropriate control of the air flow the gases cool quickly to allow a carrier in the liquid (usually propylene glycol or glycerol), to condense into microscopic droplets which are visible as a dense smoke-like aerosol which is provided to a user.

As mentioned above, such electronic cigarettes have significant benefits in view of their non-combustible generation of an aerosol, allowing users to use them in areas where regular cigarette use would be restricted. However, variance in the air flow or ageing of the liquid can lead to problems in terms of delivering an appropriate quality of aerosol to a user. It can also be difficult for the user to control the level of intensity or strength of flavour that is delivered to them.

The present invention proposes, as will now be described with reference to FIGS. 3a to FIGS. 3c, a new kind of aerosol generating device such as an electronic cigarette 10 in a first preferred embodiment, which overcomes some of these problems. In these figures components which correspond to those in the earlier figures are numbered identically. For simplicity of illustration, certain components have been removed from illustration, such as the porous metal bridge 4 and transfer element 5, as well as switch 7, although these may well be present dependent upon particular end consumer requirements, as will be appreciated by a person skilled in the art.

Figure 3A:
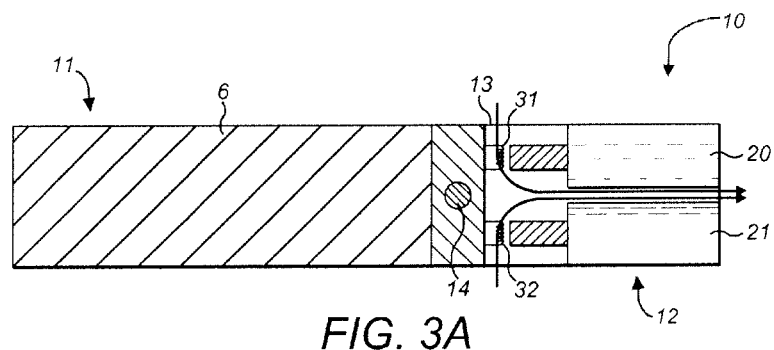
FIGS. 3A to 3C are schematic diagrams of example reservoir components for electronic cigarettes according to the present invention.

Referring to FIG. 3a, the electronic cigarette 10 of the invention comprises an elongated body 11, for instance cylindrical. At an end of said elongated body 11 a mouthpiece 12 is provided for a user to place the electronic cigarette 10 at his mouth to draw air into the electronic cigarette 10 through at least one air intake 13 to produce an aerosol that can be then inhaled. A power supply in the form of a battery 6 to provide an electrical supply to a heater assembly 3 may be accommodated by or lodged in the elongate body 11.

Compared to the electronic cigarette 1 shown in FIGS. 1 and 2, the electronic cigarette 10 of the present invention further comprises at least two liquid reservoirs 20, 21 in working arrangement with the heater assembly 3. Each reservoir 20, 21 contains an aerosol producing composition, with at least one of said reservoirs 20, 21 preferably containing a flavorant. Moreover, in this embodiment the heater assembly 3 comprises a first and a second heating elements 31, 32 for each of the two liquid reservoirs 20, 21. Both reservoirs 20, 21 are in the present embodiment located, embedded, or lodged in the mouthpiece 12 section of the body 11 of the electronic cigarette 10 and preferably contain an aerosol producing composition to produce an aerosol when air is drawn from the mouthpiece 12 of the elongate body 11 by a user.

In the embodiment of FIG. 3a, control means for supplying power from the battery 6 to the heater assembly 3 and actuation of the heating elements 31, 32 is further provided. The control means may be embedded into the elongated body 11. The control means at least comprises an electric switch 14 provided on the external surface of the elongate body 11 of the electronic cigarette 10. The control means can also comprise indicators or any kind of power supply circuitry to individually power the heating elements 31, 32. For instance, the control means can be arranged to allow alternately pulsed power supply to each of the heating elements 31, 32 of the heater assembly. Such pulsed alternate power supply of the heating elements 31, 32 can allow the user to selectively and successively produce aerosol from each of the two reservoirs 20, 21 and thereby adjust the flavour profile of the aerosol.

In operation, a user can operate the selector switch 14 to determine which of the heating elements 31, 32 is activated, and as such select which liquid from which reservoir 20, 21 is heated to provide aerosol. By provision of two reservoirs 20, 21 it is therefore possible for a user to select and adjust the aerosol that is inhaled to vary the flavour or composition in accordance with their particular needs at any moment or location.

Figure 3B:
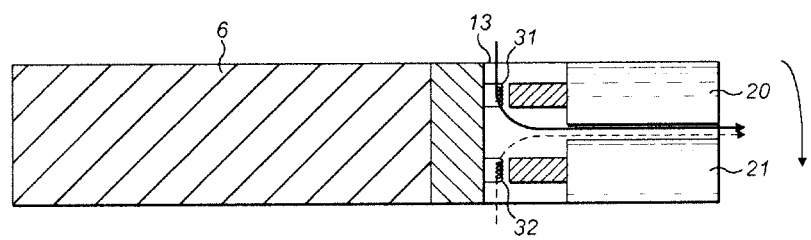

FIG. 3b shows a second embodiment of the electronic cigarette 10 of the invention, which again has two reservoirs 20, 21 located in the mouthpiece section 12 of the elongated body 11 of the electronic cigarette 10. In this case, the heater assembly 3 also comprises two heating elements 31, 32, one for each reservoir 20, 21, both being supplied by a battery 6. In that second embodiment, the control means comprises a switch which is actuated by twisting the mouthpiece section 12 of the electronic cigarette 1 which contains the reservoirs 20, 21 of the elongate body 11. This selects which of the heating elements 31, 32 is powered and the reservoir 20, 21 delivering liquid to produce an aerosol when an air flow passes through the electronic cigarette 1 when a user draws a puff from the mouthpiece section 12.

Figure 3C:
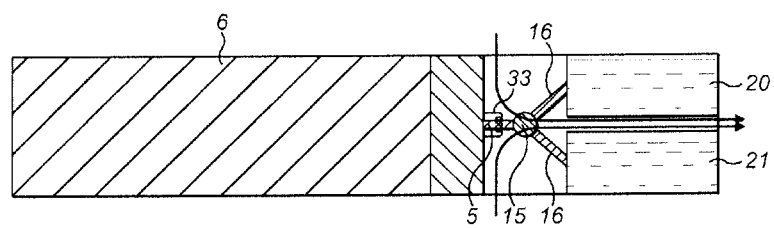

FIG. 3c shows a third embodiment of an electronic cigarette 10 according to the present invention. In that third embodiment the control means of the electronic cigarette comprises a selectable valve 15 positioned adjacent to two bridges 16 which connect to respective reservoirs 20, 21. In this example the heater assembly 3 comprises a single heating coil 33 provided with a central transfer element 5. In operation in this case, a user can move the valve 15 to select one of the two reservoirs 20, 21 delivering liquid that generates the aerosol or can select a mixture of the two to alter the level of flavour or, indeed, activate the mixing of two at the moment of inhalation to prevent negative aging effects by the two liquids being mixed too soon before aerosol generation.

The electronic cigarette 10 of the invention as depicted in FIGS. 3a to 3c can be a single use, disposable electronic cigarette or a multiple use device. In the case of a multiple-use device, the reservoirs 20, 21 can be made to be either disposable or refillable with an aerosol producing composition of a user's choice. In that case, is it preferred that the mouthpiece section 12 of the elongate body 11 of the electronic cigarette 10 is detachable from said body 11 so as to let a user access the reservoirs 20, 21 to either replace or refill it. The mouthpiece 12 section itself can also be disposable for hygiene purposes. In addition, the reservoirs can eventually be positioned in the mouthpiece itself.

The battery 6 can also be a disposable battery or a rechargeable battery, preferably of a lithium ion rechargeable type as already commonly used in electronic cigarettes.

Figure 4A:
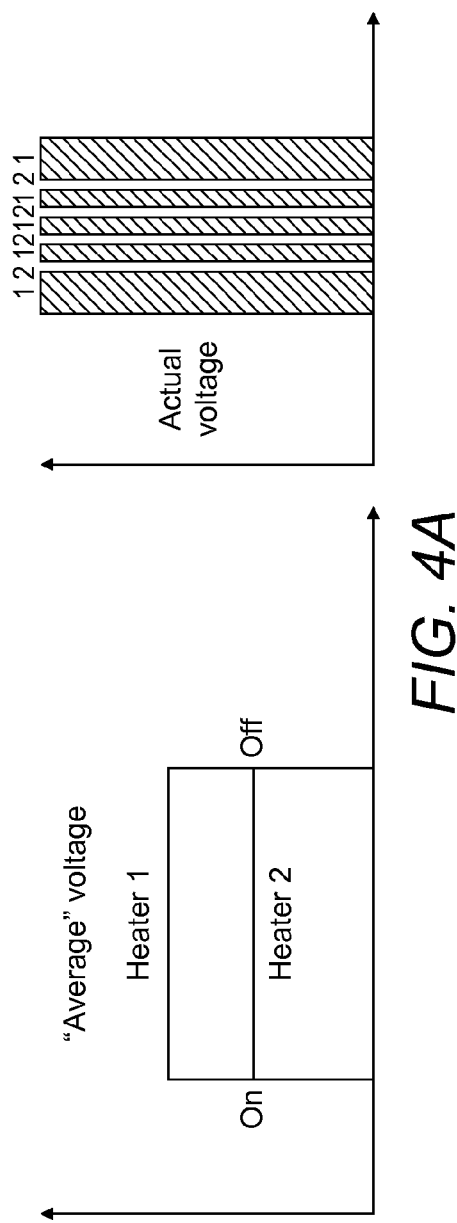
FIG. 4 shows example approaches for activating a heater assembly in the examples of FIGS. 3A to 3C.

FIG. 4 shows a number of example approaches to controlling the heating assembly of the present invention in the case of example of FIG. 3a. It will be appreciated that similar approaches could be taken when the other examples either through control of separate heating elements within the heater assembly or by control of the flow of liquid to a single heater assembly. As shown in FIG. 4a in a first example the "average" voltage applied to the two heaters is controlled so that it is different in each. The average is generated by pulsing a direct voltage applied to each heater element or by controlling the level of the voltage. In either case, as can be seen in this example, a user has selected a configuration in which a higher "average" voltage is applied to the first heater when compared to the second heater, enabling a roughly 60/40 portion of content from the two reservoirs to be used to generate an aerosol for inhalation by a user.

Figure 4B:
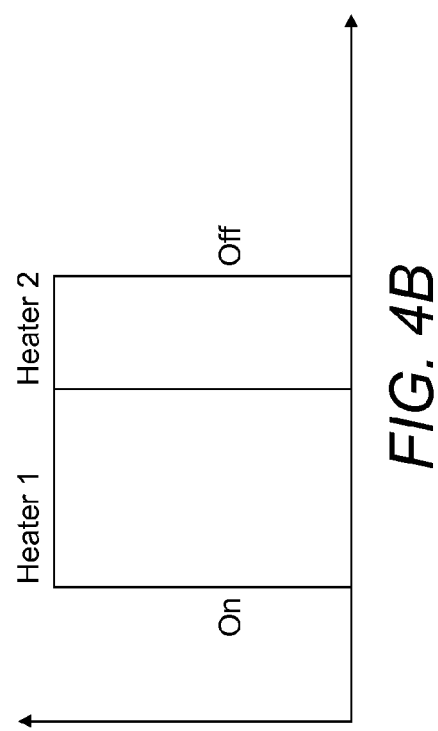
Figure 5C:
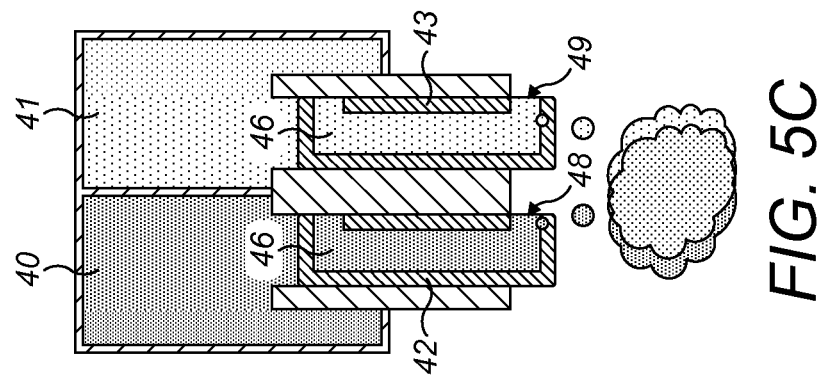
FIG. 5 is a schematic diagram showing a further example of the present invention and its operation.
Figure 5B:
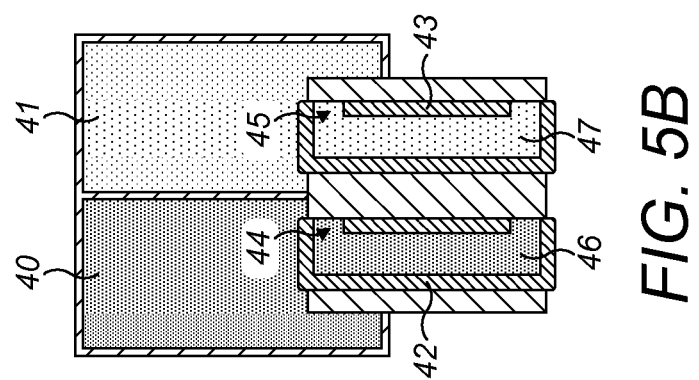
Figure 5A:
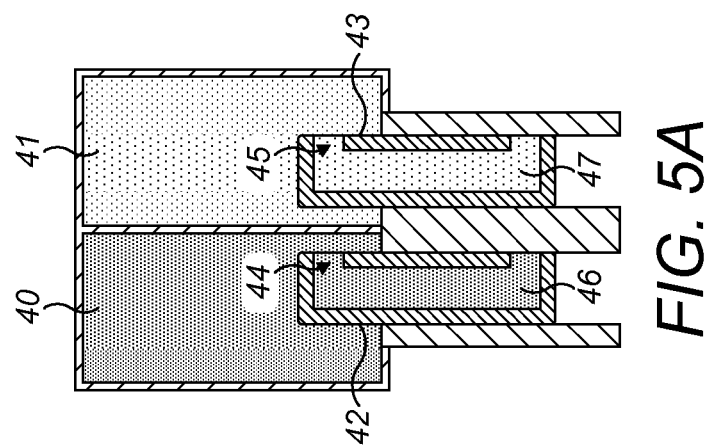
Figure 6C:
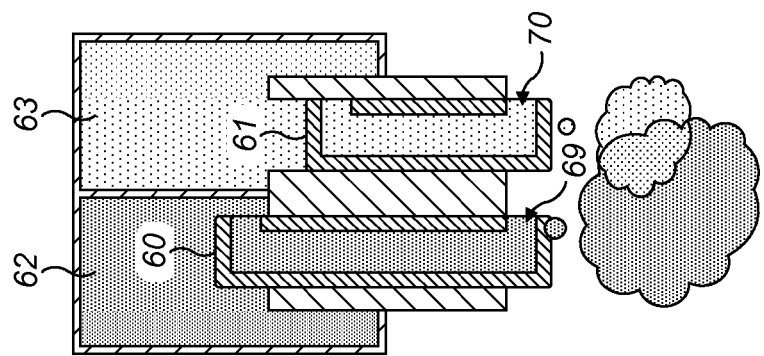
FIG. 6 is a schematic diagram showing a further example of the present invention and its operation.
Figure 6B:
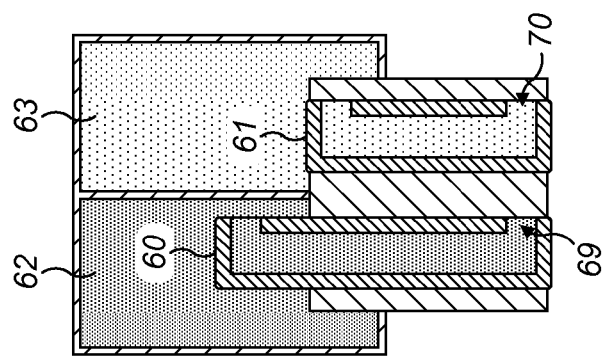
Figure 6A:
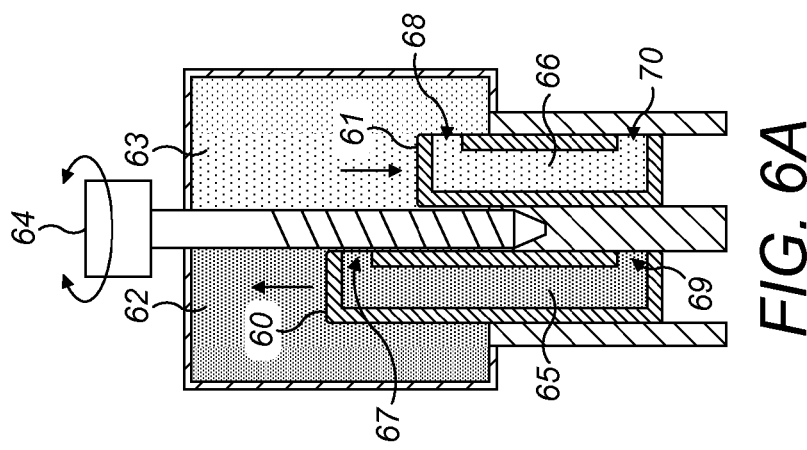
Figure 7:
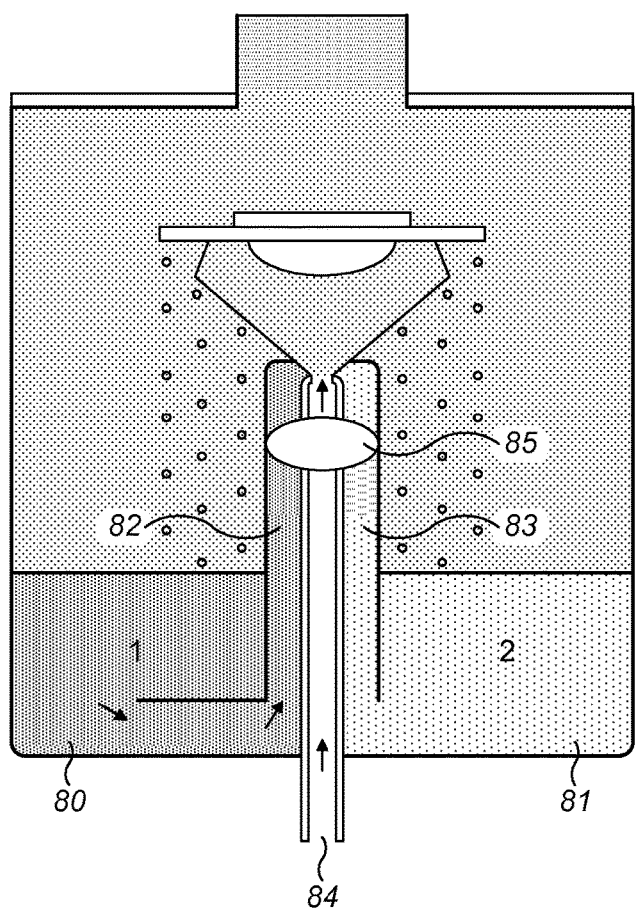
FIG. 7 is a schematic diagram showing a further example of the present invention.

FIG. 4*b* shows a second example in which a first heater is supplied with current for a first period, and then switched off and the second heater element supplied. This enables the user to control the nature of the aerosol during an inhalation.

With all the examples of the present invention, switching of supply to the battery may be provided by a user-activated switch or by an inhalation-activated switch, dependent upon consumer need.

FIG. 5 shows a further example of an aerosol generating device according to the present invention in the form of a non-heated aerosol generating device. In this example the device of the invention again enables a user to control more readily the aerosol that they inhale and also enabling the fresher mixing of components at the time of inhalation.

As can be seen from FIGS. 5A, 5B and 5C, a container is subdivided into two sections 40, 41, each of which contains a different fluid under pressure.

Furthermore, a first and a second valves 42, 43 are also provided and are respectively in fluid engagement with sections 41, 42 through openings 44, 45. First and second valves 42, 43 have respective chambers 46, 47 which receive fluid from sections 40, 41 for subsequent dispensing to a user when the device is operated via an aperture 48, 49 (see FIG. 5C). The valves 42, 43 are configured such that they are selectively operable by a user through a mechanism (not shown) to operate either the first valve 42 on its own, the second valve 43 on its own, the first and second valves 42, 43, together, or one of the two valves followed by the other in sequence. Thus, each of the valves 42,43 may be arranged to provide a predetermined amount of its respective composition or compound. This enables a user to collectively dispense the contents of the chambers 46, 47 individually, together or in sequence to control the flavour of the aerosol that they inhale.

FIG. 6 shows an adaptation of the configuration of FIG. 5, in which two valves 60, 61 are provided for a user to selectively control the release of fluid from two reservoirs 62 and 63. Each valve 60, 61 has an internal metering chamber 65, 66 in fluid communication with the reservoirs 62, 63 through apertures 67, 68. In addition, each valve 60, 61 further has a discharge opening 69, 70 to release a dose of fluid from each reservoirs 62, 63 to form an aerosol.

In this example an adjustment mechanism 64 is provided which engages with either one or both of the valve mechanisms 60, 61 of one or more of their respective chambers 62, 63. Actuation of component 64 by a user and therefore adjustment of the relative sizes of the chambers 65 and 66 is possible for a user to select the proportions of the doses of fluid provided from the reservoirs 62, 63 when the user operates the device to receive the aerosol.

FIG. 7 shows a schematic diagram showing a further example of an aerosol generating device according to the present invention in the form of a nebuliser. In this example two liquids are provided 80, 81 in separate compartments and pass through respective conduits 82, 83. A means for drawing the compositions or compounds from the compartments or reservoirs may be a source of high pressure gas. A gas inlet 84 is provided, but this time the flow of the liquids 80, 81 and gas passing through the gas inlet 84 is controlled by a valve 85 to enable control of the relative proportions of the liquids 80, 81 which are mixed with the gas to form the aerosol. Again, a user controls the flow of aerosol by controlling the supply of gas to the valve 85, but in this example of the present invention, as with others, the user is able to control the relative mixing of the liquids 80 and 81 to control the nature of the aerosol that is inhaled in accordance with their wishes.

As mentioned above, all of the examples of the present invention enable the provision of an aerosol-generating device with improved consumer experience through the ability of the consumer to control more readily the aerosol that they inhale, as well as also enabling the provision of "fresher" mixing of the components of the aerosol generating liquid.

The invention claimed is:

1. An electronic cigarette comprising:

at least two reservoirs, each arranged to contain a separate aerosol producing composition wherein at least one of the reservoirs includes a flavorant;

means for drawing the compositions from the reservoirs to generate an aerosol for inhalation for a user; and means for mixing the compositions after they have been drawn from the reservoirs, the mixing means being arranged to allow a user to select the relative proportions of the two compositions in the aerosol, wherein the means for mixing comprises a user actuated valve which can be operated to selectively connect each of two or more of the reservoirs to a transfer element forming part of at least one heater assembly.

2. The electronic cigarette according to claim 1, further comprising:

a power source;

means for selectively supplying power from the power source to the heater assembly; and control means for selectively controlling the heating of the composition from one or more of the reservoirs by the heater assembly, such that, when power is supplied to the heater assembly together with the selected the composition, an aerosol is generated for inhalation by a user.

3. The electronic cigarette according to claim 2, wherein the means for selectively supplying power from the power source to the at least one heater assembly is a switch activated by a user drawing air through the aerosol-generating device.

4. The electronic cigarette according to claim 2, wherein the at least one heater assembly comprises a heating element associated with each reservoir, and the control means is arranged such that a user can select the amount of power to be applied to each heating element to thereby control the amount of the composition from each reservoir that is used to generate the aerosol.

5. The electronic cigarette according to claim 4, wherein the control means is arranged to allow alternate pulsed power supply to each heating element of the heater assembly.

6. The electronic cigarette according to claim 2, wherein the at least one heater assembly has a heating element associated with each reservoir and the control means comprises a valve for controlling the flow of air over each heating element, thereby controlling the amount of the composition that is used from each reservoir to generate the aerosol.

7. The electronic cigarette according to claim 2, further comprising an elongated body into which said reservoirs and said control means are embedded, said elongated body further comprising at least one air intake and at least one mouthpiece section for a user to draw air inside the elongated body to mix with said aerosol and to inhale the mixed aerosol composition through the mouthpiece.

8. The electronic cigarette according to claim 2, further comprising an elongated body including a mouthpiece for a user to draw air inside the elongated body, wherein the power source is lodged in said elongated body and the at least one heater assembly and the at least two reservoirs are lodged in the mouthpiece of the elongated body.

9. The electronic cigarette according to claim 1, wherein the reservoirs are arranged to hold the compositions under pressure.

10. The electronic cigarette according to claim 1, wherein the means for drawing the compositions from the reservoirs is a source of high pressure gas; and wherein the means for enabling a user to control the relative proportions of the compositions is a variable proportion valve.

11. The electronic cigarette according to claim 1 wherein the reservoirs are refillable.

12. A mouthpiece portion for an electronic cigarette, the mouthpiece comprising:
- at least two reservoirs, each arranged to contain a separate aerosol producing composition wherein at least one of the reservoirs includes a flavorant;
- means for drawing the compositions from the reservoirs to generate an aerosol for inhalation for a user; and
- means for mixing the compositions after they have been drawn from the reservoirs, the mixing means being arranged to allow a user to select the relative proportions of the two compositions in the aerosol,
- wherein the means for mixing comprises a user actuated valve which can be operated to selectively connect each of two or more of the reservoirs to a transfer element forming part of at least one heater assembly.

* * * * *